(12) United States Patent
Harris et al.

(10) Patent No.: US 6,797,738 B2
(45) Date of Patent: Sep. 28, 2004

(54) OPEN PORE BIODEGRADABLE MATRICES

(75) Inventors: Leatrese Harris, Flint, MI (US); David J. Mooney, Ann Arbor, MI (US); Lonnie Shea, Evanston, IL (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/939,714

(22) Filed: Aug. 28, 2001

(65) Prior Publication Data

US 2002/0045672 A1 Apr. 18, 2002

Related U.S. Application Data

(63) Continuation of application No. 09/402,119, filed as application No. PCT/US98/06188 on Mar. 31, 1998, now Pat. No. 6,281,256.
(60) Provisional application No. 60/042,198, filed on Mar. 31, 1997.

(51) Int. Cl.[7] .................................................. C08J 9/26
(52) U.S. Cl. ........................... 521/149; 521/51; 521/61; 521/63; 521/123; 521/182; 521/183; 521/189
(58) Field of Search .............................. 521/51, 61, 63, 521/123, 149, 182, 183, 189

(56) References Cited

U.S. PATENT DOCUMENTS

| | | | |
|---|---|---|---|
| 2,819,981 A | | 1/1958 | Schomstheimer et al. |
| 2,835,607 A | | 5/1958 | Segner |
| 3,770,537 A | | 11/1973 | Elton |
| 4,461,876 A | | 7/1984 | Lieberman et al. |
| 4,636,526 A | * | 1/1987 | Dorman et al. ............. 521/106 |
| 5,041,138 A | | 8/1991 | Vacanti et al. |
| 5,567,612 A | | 10/1996 | Vacanti et al. |
| 5,618,853 A | * | 4/1997 | Vonken et al. ................ 521/60 |
| 5,696,175 A | | 12/1997 | Mikos et al. |
| 5,709,854 A | | 1/1998 | Griffith-Cima et al. |
| 5,847,012 A | * | 12/1998 | Shalaby et al. ............... 521/61 |
| 6,281,256 B1 | * | 8/2001 | Harris et al. ................ 521/123 |

* cited by examiner

*Primary Examiner*—John M. Cooney, Jr.
(74) *Attorney, Agent, or Firm*—Millen, White, Zelano & Branigan, P.C.

(57) ABSTRACT

The invention is directed to a process for preparing porous polymer materials by a combination of gas foaming and particulate leaching steps. The invention is also directed to porous polymer material prepared by the process, particularly having a characteristic interconnected pore structure, and to methods for using such porous polymer material, particularly for tissue engineering.

35 Claims, 8 Drawing Sheets

OPEN PORE BIODEGRADABLE MATRICES

This application is a Continuation Application of U.S. Ser. No. 09/402,119, filed Jun. 6, 2000 now U.S. Pat. No. 6,281,256 which is the National Stage application of PCT/US98/06,188 filed Mar. 31, 1998 which claims benefit of provisional application 60/042,198 filed Mar. 31, 1997.

This application claims priority benefit of U.S. Provisional Application No. 60/042,198 filed Mar. 31, 1997.

The invention is directed to a process for preparing porous polymer materials by a combination of gas foaming and particulate leaching steps. The invention is also directed to porous polymer material prepared by the process, particularly having a characteristic interconnected pore structure, and to methods for using such porous polymer material, particularly for tissue engineering.

The lack of autologous and allogeneic tissue suitable for transplantation has driven the development of the tissue engineering field, in which new tissues are created from cultured cells and biomaterials. This is advantageous because these cells can be expanded in vitro and cultured for use by multiple patients. The biomaterial serves as a vehicle to localize the cells of interest, a physical spacer to create potential space for tissue development, and as a template guiding tissue regeneration. Biodegradable homopolymers and copolymers of lactic and glycolic acid are attractive candidates for fabricating tissue engineering matrices due to their flexible and well defined physical properties and relative biocompatability. Additionally, the degradation product of these polymers are natural metabolites and are readily removed from the body.

Several techniques have been used to fabricate polymers into porous matrices for tissue engineering applications, including solvent-casting/particulate leaching (SC/PL) (A. G. Mikos, A. J. Thorsen, L. A. Czerwonka, Y. Bao, and R. Langer, "Preparation and characterization of poly(L-lactic acid) foams," Polymer, 35, 1068-1077 (1994)); phase separation (H. Lo, M. S. Ponticiello, and K. W. Leong, "Fabrication of controlled release biodegradable foams by phase separation," Tissue Engineering, 1, 15–28 (1995)); fiber extrusion and fabric forming processing (J. F. Cavallaso, P. D. Kemp and K. H. Kraus, "Collagen Fabrics as Biomaterials," Biotechnology and Bioengineering, 43, p. 781–791 (1994)); and gas foaming. (D. J. Mooney, D. F. Baldwin, N. P. Suh, J. P. Vacanti, and R. Lager, "Novel approach to fabricate porous sponges of poly(D,L-lactic-co-glycolic acid) without the use of organic solvents," Biomaterials, 17, 1417–1422 (1996).) The solvent-casting/particulate leaching and phase separation approaches require the use of organic solvents. Residues of organic solvents which can remain in these polymers after processing may damage transplanted cells and nearby tissue, and inactivate many biologically active factors (e.g., growth factors) one might wish to incorporate into the polymer matrix for controlled release. Fiber forming typically requires high temperatures (above the transition temperature of polymer), and is not amenable to processing amorphous polymers. The high temperatures used in this process would likely denature any biologically active molecules one might wish to incorporate into the matrix.

The gas foaming method (for example, of Mooney et al., cited above) provides a technique to fabricate highly porous matrices from poly(lactic-co-glycolic acid) (PLGA) using a high pressure gas that avoids the use of organic solvents and high temperatures. However, the technique typically yields a closed pore structure, which is disadvantageous in many applications of cell transplantation. In addition, a solid skin of polymer results on the exterior surface of the foamed matrix and this may lead to mass transport limitations.

An object of this invention is to provide a new process for preparing porous polymer materials which are useful for tissue engineering and other applications wherein the pore structure is particularly advantageous. For example, the polymers of the invention may have two types of porosity, the first formed by gas-foaming processing and the second formed by the action of particulate leaching. The combination of these two porosity types can be regulated by the processing conditions and materials used to provide porous polymer materials with a range of advantageous properties. In a preferred embodiment, the porosity from particulate leaching results in interconnected pore structure materials having an open pore structure. Other objects of the invention include the porous polymer materials prepared by the process and methods using such materials for tissue engineering, for example.

Upon further study of the specification and appended claims, further objects and advantages of this invention will become apparent to those skilled in the art.

According to the process of the invention, a mixture of polymer particles and a leachable particulate material molded, optionally with compression, to a desired size and shape are subject to a high pressure gas atmosphere so that the gas dissolves in the polymer; then a thermodynamic instability is created, for example by reduction of the pressure, so that the dissolved gas nucleates and forms gas pores within the polymer; this causes expansion of the polymer particles, and as they expand they fuse, creating a continuous polymer matrix containing the particulate material; finally, the particulate material is leached from the polymer with a leaching agent creating a further porosity. The process thus provides a novel combination of the processes of gas foaming (GF) to form pores and particulate leaching (PL) to form another type of porosity. Hence, the process can be termed as a GF/PL process as opposed to the known solvent-casting/particulate leaching (SC/PL) processes.

The novel materials prepared by the process are characterized by having pores formed from gas foaming and pores formed by particulate leaching, the particulate leaching pores also being termed macropores. Preferably, the porosity resulting from the particulate leaching, which can be controlled by the amount and size of the particulate among other factors, is such that it results in interconnections and, thus, an open pore structure. Typically, matrices prepared by the GF/PL method of the invention will have an interconnecting or open pore structure akin to the structure demonstrated in the photomicrographs generated according to Example 1 and discussed therein. In one embodiment providing a mixture of polymer and leachable particulate wherein the amount of leachable particulate is at least 50% by volume will result in a partially interconnecting or open pore structure. A higher amount of leachable particulate can be used to obtain a fully interconnected structure.

While materials prepared by an SC/PL process can also provide some extent of an interconnected pore matrix, the inventors have discovered that the materials prepared by the inventive GF/PL process exhibit a distinct pore structure and significantly advantageous mechanical properties over SC/PL prepared materials. This advantage is in addition to the advantage of the absence of necessity for organic solvents and/or high temperatures in preparation of the material and the absence of organic solvent residue in the prepared materials, which advantages make the materials even more useful for the applications described below. For example, the materials of the invention exhibit much higher strength properties, e.g. tensile strength. For instance, the materials according to the invention can be prepared to maximize the tensile strength to provide materials with a tensile modulus of, for example, 850 kPa, particularly 100 kPa, or higher. Although, such high strength materials may not be required for all applications and materials with a tensile modulus as low as 100 kPa, for example, have been found to be useful. Further, the materials exhibit improved compression resistance. For instance, the materials according to the invention can be prepared to maximize the compression resistance to provide materials with a compression modulus of, for example, 250 kPa, particularly 289 kPa, or higher. Comparative SC/PL prepared materials exhibit a tensile modulus of about 334±52 kPa and a compression modulus of about 159±130 kPa.

While not intending to be bound by this theory, it is reasonably hypothesized that the improved mechanical properties and stronger matrix of the materials prepared by the inventors' GF/PL process result, at least in part, from greater uniformity of polymer distribution in the materials and/or greater uniformity in size and distribution of porosity in the materials. SC/PL prepared polymers will not have such a uniform pore structure because the solvent evaporates from the polymer in a non-uniform manner and thus the polymer concentration changes non-uniformly in the material. For instance, SC/PL materials typically have non-uniformity because as the solvent evaporates the polymer concentration increases at the bottom of the matrix, i.e. the area where the matrix touches the glass cover slip. In contrast, the GF/PL materials exhibit a very uniform pore structure indicating that the polymer foams uniformly throughout the particulate bed during the gas-foaming step.

Alternatively, it is hypothesized that in the GF/PL process the mechanical properties may be enhanced by tensile alignment of the polymer chains may be occurring during the elongation which occurs during foaming. (Principles of Tissue Engineering, Academic Press, p. 264 (1997).

In any event, it is of great advantage in tissue engineering and other applications that the materials of the invention can be prepared for maximizing of tensile strength and compression resistance since they can be handled and manipulated without mechanical breakdown more readily and survive better in the environment in which they are used without mechanical breakdown. Further, the materials of the invention with both types of porosity, preferably with interconnecting porosity, provide a unique and advantageous material for many applications. The process can provide materials with a total porosity of, for example, from above 0 to 97% or higher. Preferably, the total porosity ranges from 90–97%.

For the process, a mixture of polymer and particulate material is used. The mixture is preferably as uniform as possible and can be provided by conventional means. Preferably, the mixture is molded, for example by compression molding at room temperature or other suitable temperature to effect the molding, to the size and shape which is substantially the same as that desired for its ultimate use.

The polymer and particulate materials should be selected so that the particulate can be leached with a leaching agent which does not dissolve the polymer or otherwise adversely impact on the material. Polymers and particulates useful for the SC/PL processes discussed herein are generally useful for the GF/PL process of the invention. Further useful materials are discussed below.

Any polymer into which gas can be dissolved and pores formed thereby and in which a particulate can be incorporated and leached therefrom can be used in the process. It is preferred, to facilitate dissolution of the gas, that the polymer be an amorphous or predominantly amorphous polymer. However, if it is desired to use a crystalline polymer the crystallinity can be reduced to a level such that the gas can be dissolved therein and then the crystallinity restored after formation of the pores. Depending upon the application of the materials, the polymer may be selected to be biodegradable or non-biodegradable. For many applications, such as tissue engineering, the polymer preferably is biocompatible to the environment in which it is used. A preferred useful class of polymers are homopolymers and copolymers of lactic acid and glycolic acid, for example, poly-L-lactic acid (PLLA), poly-D,L-lactic acid (PDLLA), polyglycolic acid (PGA) and copolymers of D,L-lactide and glycolide (PLGA), particularly with 50% or more of the lactide in the copolymer. Although under many conditions copolymers are preferred over homopolymers, homopolymers may be preferred in some circumstances. Other useful polymers, for example, are aliphatic polyesters, such as polyhydroxybutyrate, poly-∈-caprolactone. Further, polyanhydrides, polyphosphazines, polypeptides may be used.

Additionally, blends of different polymers may be used or polymers which contain other agents, particularly which effect the mechanical properties of the resulting matrix. For example, blends of differing PLGA polymers which have distinct properties can be used to take advantage of the properties of both. Also, other polymers can be blended with the PLGA polymers, particularly for modifying the mechanical properties thereof. For instance, a blend of a PLGA polymer and alginate material was found to provide a tougher matrix with greater elasticity and ability to withstand greater strain before breaking. Thus, it can be useful, depending on the application, to blend polymers which result in a matrix with better pliability and/or strength. Blends with materials which act as plasticizers, toughening agents or modifiers of other properties are, therefore, useful in the invention. These materials can either be polymers or smaller molecule agents which may act in a temporary manner and then diffuse from the matrix.

The polymer composition and molecular weight also had a large affect on the three dimensional matrices' porosity and mechanical properties. Copolymers of PLGA were shown to foam to a much greater extent than either homopolymer PGA or PLLA. This finding is consistent with previous reports that the amorphous PLGA copolymers foam more than does the crystalline polymer PGA (Mooney et al., *Biomaterials,* 17, 1417–1422, 1996). This is likely due to an increased gas dissolution in amorphous polymers as compared to crystalline polymers (D. F. Baldwin et al., *J.Eng. Mat. Tech.,* 117, 62, 1995; and D. W. Van Krevelen, *Properties of Polymers,* Elsevier Publ., 1976). The molecular weight of the polymer has a large effect on scaffold porosity. A polymer with a high molecular weight (large i.v.) did not form scaffolds with as high of porosity as the same polymer with a lower molecular weight. The longer polymer chains of the high molecular weight polymer likely entangle to a greater extent, thus providing a stronger resistance to expansion than the shorter polymer chains.

In one preferred embodiment, maximal pore formation can be achieved by use of a low molecular weight amorphous copolymer of lactide and glycolide. These matrices will likely have great utility in the regeneration of oral tissues. They may be used alone as a GTR matrix. They may also be utilized to deliver growth factors in a sustained, local manner to promote regeneration. In addition, they could be used to transplant cells directly to a site to promote tissue regeneration from these cells and interacting host cells.

The leachable particulate is any particulate material which can be leached from the polymer matrix with a leaching agent. Preferred are salts soluble in an aqueous medium, preferably water. As salts, NaCl, Na citrate, Na tartrate, and KCl are useful particulate materials. Other useful particulates leachable by dissolution include, for example, gelatin, collagen and alginate particulates. It is also possible to use particulates which are leachable by organic solvents where the solvent does not adversely effect the polymer, however, this is not preferred since such would mitigate the advantage of lack of need for an organic solvent and lack of residue in the product. As discussed above, the size of the particulate will affect the size of the pores formed upon leaching of the particulate. Although not limiting of the invention, it is preferred that the particulate has an average size of from 10 to 500 microns. This size will correspond approximately to the size of the pores formed by the leaching thereof.

A gas is dissolved in the polymer of the, preferably molded, mixture of polymer and particulate by subjecting the mixture to a pressurized atmosphere of a gas which is inert to the system and will dissolve in the polymer under suitable conditions. Suitable gases and conditions are known from other gas-foaming processes, such as discussed in the Biomaterials article above, and they can generally be used herein. Preferred examples of suitable gas include $CO_2$, air, nitrogen, helium, neon, krypton, argon, xenon or oxygen. Also volatile liquids which provide a gas at the gas foaming temperature may be used, e.g. water. However, other gases or volatile liquids which form gases known to be useful as blowing agents may also be used. These include, for example, fluorinated, including perfluorinated, hydrocarbons. Preferred for these are aliphatic or cycloaliphatic fluorinated hydrocarbons of up to 8 carbon atoms such as trifluoromethane, difluoromethane, difluoroethane, tetrafluoroethane, heptafluoroethane, perfluoropropane, perfluorobutane, perfluorocyclobutane, perfluoropentane, perfluorohexane, perfluoroheptane, pefluorooctane, perfluorocyclopentane, perfluorocyclohexane, hexafluoropropane and heptafluoropropane. Sulfur hexafluoride may also be a useful blowing agent. Other known blowing agents include alkanes such as propane, butanes and pentanes; cycloalkanes and cycloalkenes such as cyclobutane, cyclopentene and cyclohexene; dialkyl ethers such as dimethyl ether, methyl ethyl ether and diethyl ether; cycloalkylene ethers such as furan; ketones such as acetone and methyl ethyl ketone; and carboxylates such as formic acid, acetic acid and propionic acid.

The pressure is selected to facilitate dissolution of gas into the polymer and will, thus, depend upon the gas used, the polymer used and the temperature. Pressures of from about 600 to 900 psi are generally useful for $CO_2$ and PLGA polymers, although not limiting on the invention. For example, gases at super- or subcritical conditions can even be used. Furthermore, a volatile liquid which can be dissolved in the polymer and forms a gas upon imposition of the thermodynamic instability can be used. As an example, $CO_2$ can be dissolved in a mixture of poly[D,L-lactic-co-glycolic acid] polymer and NaCl particulate at a pressure of about 800 psi applied for about 48 hours to allow saturation.

The specific gas used in foaming can be a critical variable in production of porous matrices. The choice of gas used in foaming has a large effect on the final scaffold structure. $CO_2$ produced highly porous matrices, whereas $N_2$ and He led to no measurable pore formation. These results are consistent with a number of previous studies in which $CO_2$ has been used to create porous polymer structures (Mooney et al., *Biomaterials,* 17, 1417–1422, 1996). While the exact mechanism underlying this result is not known, the greater degree of foaming experienced with $CO_2$ as compared to both N2 and He may be the result of a specific interaction between $CO_2$ and the carbonyl groups of PLGA (Kazarian et al., J. Am. Chem. Soc, 118, 1729–1736, 1996).

The gas equilibration time and pressure release rate affected the porosity and stability of the matrices, although not as strongly as the other variables.

In order to initiate nucleation of the dissolved gas and growth of gas pores in the material, a thermodynamic instability is created. This phenomenon is described for example by Park, Baldwin and Suh, "Effect of the Pressure Drop Rate on Cell Nucleation in Continuous Processing of Microcellular Polymers," Polymer Engineering and Science, 35, pp. 432–440 (1995). Preferably, this is done by lowering the pressure of the gas atmosphere, for example, down to atmospheric pressure over a short time period. The time period being, for example, from a few seconds to about 15 minutes. The gas phase separates from the polymer via pore nucleation and growth of the pores occurs through diffusion of gas into areas adjacent the nucleation sites. The pore growth in turn reduces the polymer density. Other methods for creating the instability, such as raising the temperature, may be used, but, are not preferred due to ease of processing. The pore structure and pore size of the gas pores formed will be a factor of, among others, the type of gas used, the amount of gas which will depend upon temperature and initial and final pressure of the gas atmosphere applied, the solubility of the gas in the particular polymer, the rate and type of pore nucleation and the diffusion rate of the gas through the polymer to the nuclei. These and other factors can be adjusted to provide gas pores of a suitable size. Sufficient gas should be dissolved to cause formation of a continuous polymer matrix when the polymer expand during gas pore growth.

As a result of the thermodynamic instability, pore nucleation and gas pore formation and expansion, the polymer containing the particulate material forms a continuous phase, i.e matrix, around the gas pores.

The particulate is leached from the polymer with a leaching agent. Useful as leaching agent is any agent which will leach, e.g., dissolve and remove, the particulate from the polymer. As discussed above, an aqueous-based leaching agent, particularly water, is preferred. The leaching of the particulate from the polymer forms the type of porosity, other than that formed by the gas-foaming, which as discussed above can provide for an interconnecting pore structure.

The following embodiment is provided as a representative, non-limiting, example of the invention.

Discs comprised of polymer (e.g., poly[D,L-lactic-co-glycolic acid]) and NaCl particles were compression molded at room temperature, and subsequently allowed to equilibrate with high pressure $CO_2$ gas (800 psi). Creation of a thermodynamic instability led to the nucleation and growth of gas pores in the polymer particles, and the formation of a continuous polymer matrix. The NaCl particles were subsequently leached to yield macropores, and a macropore structure. The overall porosity and level of pore connectivity was regulated by the ratio of polymer:salt particles. Both the compressive modulus (159±130 kPa for SC/PL vs. 289±25 kPa for GF/PL) and tensile modulus (334±52 kPa for SC/PL vs. 1100±236 kPa for GF/PL) of matrices formed with this were significantly greater than those formed with a standard solvent casting/particulate leaching process. The potential of these matrices for engineering new tissue was demonstrated by finding that smooth muscle cells readily adhered and proliferated on these matrices, forming new, high density tissues ($3 \times 10^7$ cells/ml) in culture. This novel process, a combination of high pressure gas foaming and particulate leaching techniques, allows one to fabricate matrices from biodegradable polymers with a well controlled porosity and pore structure.

The materials prepared by the process of the invention exhibit a wide range of utilities. They may be applied to any use which requires a porous polymeric material, particularly with an open pore structure. Further, the materials are particularly applicable for uses wherein organic solvent residue is not tolerable, e.g. in applications wherein biocompatability is desired. For instance, the materials are useful as matrices in which cells are compatible and grow to achieve their intended function, such as in tissue replacement, eventually replacing the matrix depending on its biodegradability. Furthermore, the materials can be used to provide matrices already bound to cells which may then be surgically implanted into a body. Further, the materials can be used as a sustained release drug delivery system, as wound healing matrix materials, as matrices for in vitro cell culture studies or uses similar thereto. The stable structure of the materials of the invention provide ideal cell culture conditions.

The materials of the invention prepared by the GF/PL process generally further have applications similar to those of materials prepared by the SC/PL and phase separation techniques, for example, in a variety of cell transplantation applications, including for hepatocytes (D. J. Mooney, P. M. Kaufmann, K. Sano, K. M. McNamara, J. P. Vacanti, and R. Langer, "Transplantation of hepatocytes using porous biodegradable sponges," Transplantation Proceedings, 26, 3425–3426 (1994); D. J. Mooney, S. Park, P. M. Kaufmann, K. Sano, K. McNamara, J. P. Vacanti, and R. Langer, "Biodegradable sponges for hepatocyte transplantation," Journal of Biomedical Materials Research, 29, 959–965 (1995)), chondrocytes and osteoblasts. S. L. Ishaug, M. J. Yaszemski, R. Biciog, A. G. Mikos; "Osteoblast Function on Synthetic Biodegradable Polymers", J. of Biomed. Mat. Res., 28, p. 1445–1453 (1994). However, the materials of the invention have better mechanical properties and avoid the problem of organic solvent residue that may damage transplanted or migrating cells and nearby tissue and/or inactivate biologically active factors.

Smooth muscle cells readily adhere to the matrix material of the invention and create three-dimensional tissues within these porous structures; thus, they provide a suitable environment for cell proliferation. In vitro experiments indicate concentrated cell growth around the periphery of the matrix. This is likely due to $O_2$ diffusion limitations to the cells at the center of the matrix because of the thickness (3.4 mm) of the sponge.

In addition, these matrices have a better potential to incorporate growth factors than those prepared using organic solvents. The potential problem with organic solvents is that residue remains in these polymers after processing may damage the transplanted cells and nearby tissue. Further, exposure to organic solvents would inactivate many biologically active factors. Currently, incorporation of growth factors with biomaterials are done using microspheres. This method also uses organic solvents during fabrication. This disadvantage can be eliminated with the matrix materials of the invention because the growth factor can be incorporated directly into the polymer matrix to obtain a better release.

One preferred manner of incorporating growth factors in a matrix for tissue engineering and/or cell proliferation is to provide a growth factor contained within a polymeric structure in particle form, e.g. as beads microspheres, or blended with another polymer or other molecules, before adding to the PLGA for foaming. The polymeric structure can be formed of another copolymer of PLGA which degrades at a different rate than the PLGA utilized to form the bulk of the matrix or from a different polymer material, such as an alginate or modified alginate material. Such a system provides an additional level of control over the release kinetics of molecules from the matrices, and additional control over their bioactivity because the growth factors contained within the polymeric structure can be designed to provide a controlled release effect therefrom in addition to the release kinetics provided by the matrix. The release is this situation will likely be controlled by either disassociation of the factor from the bead, release from the PLGA, or both. Thus, a high degree of control over release kinetics is provided over a potentially wide range. Further, multiple factors can be included in a matrix (in multiple types of the described particles and/or in polymer comprising the bulk of matrix) which will release at varying times. This will be useful if we want a cascade of growth factor release, or waves of release of the same factor (e.g., for use in immunizations). Incorporation of the growth factors into these particles (e.g., alginate beads) is also more suitable for maintaining the long-term bioactivity of the factors than if they were immobilized directly in the polymer comprising the bulk of foamed matrix.

Highly porous matrices, for example, from PLGA, with a combination of gas foaming and particulate leaching can be prepared by the invention. The method avoids the use of organic solvents or high temperatures and yields materials with desirable pore structures. It is possible to control the porosity and pore structure of these matrices by varying the particulate polymer ratio and particulate particle size for example. These matrices exhibit enhanced mechanical properties, and can be utilized to form three-dimensional tissues. This novel fabrication method can be used, for example, as an approach for drug and/or growth factor incorporation into polymers used as tissue engineering matrices.

Another useful application for the polymer matrices of the invention is for guided tissue regeneration (GTR). This application is based on the premise that progenitor cells responsible for tissue regeneration reside in the underlying healthy tissue and can be induced to migrate into a defect and regenerate the lost tissue. A critical feature of matrices for GTR is the transport of cells into the matrix, a property which is dictated by the pore size distribution and pore continuity, i.e., interconnectivity. The matrix must allow the desired cells to invade the matrix while preventing access to other cell types.

The materials of the invention, particularly as a polymer sponge made of poly(lactic acid) PLA, poly(glycolic acid) (PGA), or poly(lactic-co-glycolic acid) (PLGA), having an impermeable layer on one side can provide this selective permeability feature. The impermeable layer is composed of the same polymers but without the extent of porosity, and a variety of methods can be used to couple the impermeable layer to the polymeric sponge.

In a particular embodiment which is representative of this utility, the polymeric sponge is created by grinding PLGA followed by sieving to obtain particles with a diameter between 108 and 250 microns. These polymeric particles are mixed with sodium chloride and pressed into shape with a die at a pressure of approximately 1500 psi. The polymer/salt solid is then foamed by placing the solid in a pressure bomb and exposing it to $CO_2$ at a pressure of 800 psi for 48 hours followed by a relatively rapid reduction in pressure. This reduction in pressure produces thermodynamic instabilities in distribution of $CO_2$ causing pore formation. The polymer/salt solid is then placed in water for 24 hours to leach out the salt. Note that the water is changed during the leaching process. This process produces a polymer sponge that is greater than 95% porous. The degradation rate of the sponge can be modified by varying the composition of lactic and glycolic acid.

An impermeable layer can be created on one side of the sponge by one of the following techniques, preferably performed before gas foaming of the material. The sponge can be pressed into shape on a layer of PGA at a temperature greater than the melting temperature for PGA. The melted PGA will be able to adhere to the sponge thus forming a thin layer. This layer is impermeable because the foaming process and the leaching process have a negligible effect on pure PGA. An impermeable layer of PLGA can also be created on the sponge by pressing the sponge onto a layer of PLGA. Spraying a solution of PLA in chloroform onto one side of the sponge can also create an impermeable layer. Further, it is possible to use the same polymer material and alter the amount of leachable particulate in each section so that one section forms an open pore structure and one does not. Also, by using different polymers, materials wherein one section foams, and the impermeable layer section does not, can be provided. Although PLGA does foam following release of pressure from the bomb, an impermeable skin forms on the thin layer of PLGA which remains intact during the leaching process. Alternatively, following the foaming and leaching process, the polymeric sponge can be dipped in either melted PGA or in a solution of PLGA in chloroform. These procedures can be used to create a sponge which has a porosity of greater than 95% with an impermeable side.

Similar methods can be applied to analogous materials, as discussed above, to provide other sponge materials according to the invention useful for GTR applications.

The PLGA matrices also can provide a suitable substrate for bone formation. A critical feature of a matrix for replacement of bony tissues is its ability to provide an appropriate environment for tissue development and matrix mineralization. The ability of the GF/PL matrices to allow cell adhesion and tissue formation was assessed in vitro by seeding and culturing MC3T3-E1 cells, an osteogenic cell line, on PLGA scaffolds with techniques previously optimized for other cell types (Kim et al., *Biotech. Bioeng.*, 57, p. 46–54, 1998). Cells adhered to the GF/PL matrix, proliferated, and began secreting extracellular matrix proteins, and by 4 weeks in culture patches of mineralization could be observed. A new tissue with large areas of mineralization was formed by 6 weeks. There was no observed change in the size and shape of the matrices over this time period suggesting they had sufficient mechanical properties to control gross formation of engineered bone tissue.

A critical feature of the matrix for use in guided tissue regeneration is the ability of cells to migrate into the matrix. Preliminary experiments confirm cells readily migrated into and throughout the matrix in vitro. This was expected as previous studies with these types of matrices demonstrated fibrovascular ingrowth in vivo at a rate of 0.1–0.3 mm/day (Mooney et al., 1994, supra).

Another potential application of these sponge materials for GTR is for the treatment of periodontal disease. Periodontal disease is characterized by the loss of attachment of the periodontal ligament to the alveolar bone. The epithelial cells of the gingiva begin to grow into the site where the periodontal ligament was attached. A sponge of the matrix material according to the invention with an impermeable side could be used to prevent the downgrowth of epithelial cells while allowing the appropriate cells to occupy the porous sponge thereby regenerating the periodontal ligament. Further guidance as to such application is provided by Shea et al., *Tissue Engineering: Fundamentals and Concepts*, Chapter III.6, "Biodegradable Polymer Matrices in Dental Tissue Engineering."

For other applications in which cells are seeded or otherwise incorporated and grown within the inventive matrices, incorporation and growth of the cells can be facilitated in a manner known in the art. Examples of such methods are provided in U.S. Pat. Nos. 5,041,138; 5,567,612; 5,696,175 and 5,709,854; all of which are incorporated herein by reference.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosure of all applications, patents and publications, cited above and below, and of U.S. Provisional Application No. 60/042,198, filed Mar. 31, 1997, are hereby incorporated by reference.

In the foregoing and in the following examples, all temperatures are set forth uncorrected in degrees Celsius and unless otherwise indicated, all parts and percentages are by weight.

EXAMPLES

Example 1

Matrix Processing

Pellets of an 85:15 copolymer of D,L-lactide and glycolide (PLGA) was purchased from Boehringer Ingelheim (Henley, Montvale, N.J., USA), and utilized to fabricate polymer matrices in all experiments. The intrinsic viscosity of the polymer was about 1.3–1.7. Polymer pellets were ground using a Tekmar grinder (Bel-Art Products, Pequannock, N.J., USA), and sieved to obtain particles ranging from 106 to 250 $\mu$m. In certain experiments the polymer particles were mixed with sodium chloride particles (Mallinckrodt, Paris, Ky., USA). The salt particles were sieved to yield a range of sizes, and the weight ratio of NaCl:PLGA masses ranged from 0 to 50. In all cases, the total mass of PLGA and NaCl was held constant at 0.8 g. The mixtures of PLGA and NaCl were loaded into a KBr die (1.35 cm in diameter; Aldrich Chemical Co., Milwaukee, Wis., USA), and compressed at 1500 psi for 1 minute using a Carver Laboratory Press (Fred S. Carver, Inc., Menominee Falls, Wis., USA) to yield solid discs (thickness=3.4 mm). The samples were then exposed to high pressure $CO_2$ gas (800 psi) for 48 hours to saturate the polymer with gas. A thermodynamic instability was then created by decreasing the gas pressure to ambient pressure. This led to the nucleation and growth of $CO_2$ pores within the polymer matrices. The NaCl particles were subsequently removed from the matrices by leaching the matrices in dd$H_2O$ for 48 hours. All processing steps were performed at ambient temperature.

Porous sponges were also fabricated using a previously described solvent casting-particulate leaching technique. (A. G. Mikos, A. J. Thorsen, L. A. Czerwonka, Y. Bao, and R. Langer, "Preparation and characterization of poly(L-lactic acid) foams," Polymer, 35, 1068–1077 (1994).) In this process, PLGA was dissolved in chloroform (Malinckrodt; Paris, Ky., USA) to yield a solution of 10% (w:v), and 0.12 ml of this solution was loaded into Teflon cylinders (diameter 0.5 cm; Cole Parmer) packed with 0.4 g of sodium chloride particles sieved to a size between 250 and 500 mm. Following solvent evaporation, polymer films with entrapped salt particles (3 mm thick) were carefully removed from the molds. The salt was removed by immersing films in distilled water for 48 hrs.

Characterization

The porosity of samples was initially determined by gross measurements and weights after processing using the following equation:

$$\text{porosity}(\%) = 1 - [(\text{weight/volume})/(\text{density of polymer})] \times 100 \quad \text{Eqn. 1}$$

The samples were imaged using a scanning electron microscope (ISI-DS 130, Topcon Technologies, Pleasanton, Calif., USA). The samples were gold coated using a Sputter Coater (Desk II, Denton Vacuum, Cherry Hill, N.J., USA), and the microscope was operated at 10 kV to image the samples. Polaroid 55 film was used for the photomicrographs.

Compression and tensile testing were performed on an MTS Bionix 100 (Sintech, Research Triangle Park, N.C., USA). Samples were cut into 1×1 cm squares for compression testing. For tensile testing, the samples (1×1 cm) were attached to cardboard using epoxy glue. A 7 mm slot was cut into the center of the card board and the sample was centered, then glued to standardize the gage length. Compression and tensile tests were performed with a constant strain rate (1 mm/min). The moduli were determined from the slopes in the elastic portion of the stress-strain diagram.

Thermogravimetric analysis was utilized to determine the amount of salt residue that remained in the sponge after leaching. Matrices were heated from 150° C. to 300° C. at a constant rate of 10° C./min, and the residual mass was monitored.

Cell Studies

Smooth muscle cells (SMC) were used in all experiments. SMCs were isolated and cultured using a modification of the techniques described in Rothman et al. (A. Rothman, T. J. Kulik, M. B. Taubman, B. C. Berk, C. W. J. Smith and B. Nadal-Ginard, "Development and characterization of a cloned rat pulmonary arterial smooth muscle cell line that maintains differentiated properties through multiple subcultures," Circulation, 86, 1977–1986 (1992).) In brief, the cells were isolated from aortas of 300–350 g adult male Lewis rats (Charles River Laboratories, Wilmington, Mass., USA) using an enzymatic dissociation. After fat, adventitia, and connective tissue surrounding the arteries were removed by blunt dissection, the SM tissue was cut into multiple small pieces and placed into a spinner flask containing an enzymatic dissociation buffer at 37° C. This buffer contains 0.125 mg/mL elastase (Sigma Chemical Co., St. Louis, Mo., USA), 1.0 mg/mL collagenase (CLS type I, 204 units/mg, Worthington Biochemical Corp., Freehold, N.J., USA), 0.250 mg/mL soybean trypsin inhibitor (type 1-S, Sigma), and 2.0 mg/mL crystallized bovine serum albumin (BSA, Gibco/Life Technologies, Gaithersburg, Md., USA). After 90 minutes of incubation, the suspension was filtered through a 100 5 m Nitex filter (Tetko, Inc., Briarcliff Manor, N.Y.) and centrifuged at 200 g for 5 minutes. The pellet was resuspended in Medium 199 (Sigma) supplemented with 20% (v/v) fetal bovine serum (FBS, Gibco), 2 mM L-glutamine (Gibco), and 50 units/mL penicillin-streptomycin (Gibco). The cells were cultured on tissue culture plastic in a humidified 5% $CO_2$ atmosphere with the medium (Medium 199, 10%(v/v) fetal bovine serum, 50 units/mL penicillin-streptomycin) changed every other day. Cells at passage 17 were used in these experiments.

The matrices were seeded with SMCs by placing a 40 mL cell suspension containing $3.14 \pm 10^7$ cells/mL on top of each matrix and allowing the cell suspension to absorb into the matrix. Matrices were contained in tissue culture dishes and incubated at 37° C. for ~36 hours. Next, the polymer matrices were cultured for two weeks and placed in a spinner flask (100 mL, Bellco Glass, Inc., Vineland, N.J., USA) stirred at 40 RPM. The number of cells in the matrices was determined by measuring the DNA content in enzyme-digested triplicate samples using Hoechst 33258 dye and a fluorometer (Hoefer DyNA Quant 200, Pharmacia Biotech, Uppsala, Sweden) as previously described. For scanning electron microscopic examination, samples were fixed in 1% glutaraldehyde and 0.1% formaldehyde for 30 minutes and 24 hours, respectively, dehydrated in a graded series of ethanol/water solutions, dried, and then sputter-coated with gold. A scanning electron microscope (ISI-DS 130, Topcon Technologies) was operated at 10 kV to image samples. Histological sections were prepared by fixing cell-polymer matrices (10% formalin), dehydrating, embedding, sectioning and staining with hematoxylin and eosin or VerhoefUs using standard techniques.

Integrity and Porosity/Pore Structure of Foamed Matrices

Photomicrographs showed that gas foaming, alone, of solid polymer discs led to the formation of highly porous matrices. However, these matrices had a non-porous skin on the external surfaces and the pores were largely closed, as expected from previous studies. (D. J. Mooney, D. F. Baldwin, N. P. Suh, J. P. Vacanti, and R. Langer, "Novel approach to fabricate porous sponges of poly(D,L-lactic-co-glycolic acid) without the use of organic solvents," Biomaterials, 17, 1417–1422 (1996).) In contrast, gas-foaming and subsequent leaching of discs containing a high percentage (95%) of large (250<d<425 $\mu$m) NaCl particles, according to the invention, led to the formation of highly porous, open pore matrices with no evidence of an external, non-porous skin. The pore structure observed in cross-sections of these matrices was similar to that observed in cross-sections of matrices formed with a SC/PL technique. However, the pore structure of matrices formed from the SC/PL process is often not uniform throughout the matrix due to evaporation of the organic solvent and subs t increase in the polymer concentration of the remaining solution entrapped within the salt bed. For example, the surface of these matrices that is adjacent to the glass coverslip during processing is shown in photomicrographs to be typically less porous than the remainder of the matrix. In contrast, the pore see of gas foamed e leached (GF/PL) matrices was uniform throughout the matrix and on the exterior. TGA analysis of matrices indicated that negligible amounts of NaCl remained after leaching. There was a trace of a white residue left in the dish. To confirm that the gas foaming was responsible for the formation of stable matrices, control samples were compression molded, but not foamed. Leaching of the NaCl from these matrices led to complete breakdown of the matrices.

The ratio of NaCl:PLGA and the size of NaCl particles in GF/PL matrices were next varied to determine the range of porosity and pore structure that could be obtained with this process (Table I). The gross porosity of these matrices increased from 85.1%±2.3 to 96.5%±0.5 as the ratio of NaCl:PLGA was similarly increased. At constant NaCl (95%), the increase in salt particle diameter had very little effect on the overall porosity. However, photomicrographs showed that as the salt diameter was increased, the pore size increased in parallel.

The stability of the matrices was next assessed using compressive and tensile mechanical tests. In general, the GF/PL matrices exhibited improved mechanical properties as compared to the SC/PL matrices (See FIG. 1). The average compression moduli were 159±130 kPa and 289±25 kPa for the SC/PL and GF/PL matrices, respectively. The average tensile moduli were 334±52 kPa for the SC/PL matrices and 1100±236 kPa for the GF/PL matrices (Table II). This data represents a 80% increase in compression strength and a 300% increase in tensile strength Tissue Development on Synthetic Matrices The ability of the GF/PL matrices to allow cell adhesion and tissue formation was next assessed in an in vitro study Photomicrographs show that SMCs adhered to the GF/PL matrix and covered the available surface area following seeding. A significant increase in cell number was shown after 2 weeks in culture. The average cell density was $1.71 \times 10^7$ cells/mL and $3.05 \times 10^7$ cells/mL at 0 and 2 weeks, respectively. This is a 43.8% increase in cell density. The cells filled the pores of the matrix and created a new three-dimensional tissue within the synthetic matrix. However, most of the cell growth occurred around the periphery of the matrix in a relatively uniform manner, and a low cell concentration was observed in the center of the matrices at 2 weeks. There was no observed change in the size and shape of the matrices over this time period.

TABLE I

Gross porosity of sponges.

| NaCl Concentration (%) | Diameter (μm) | | |
|---|---|---|---|
| | 106–250 | 250–425 | >425 |
| 80 | — | 85.1 ± 2.3 | — |
| 90 | 87.3 ± 1.9 | 91.5 ± 1.4 | — |
| 95 | 93.9 ± 0.9 | 94.6 ± 0.9 | 95.0 ± 0.8 |
| 97 | — | 96.5 ± 0.5 | — |

TABLE II

Mechanical properties

| | Compressive | Tensile Test | |
|---|---|---|---|
| Method | Modulus (kPa) | Modulus (kPa) | Elongation @ break (%) |
| Solvent/leach | 159 ± 130 | 334 ± 52 | 17.5 ± 1.9 |
| Foam/leach | 289 ± 25 | 1100 ± 236 | 12.0 ± 1.3 |

Example 2

Growth Factor Release from Foamed Matrix

Method 125I-labelled vascular endothelial growth factor (VEGF) was first added to a solution of 1% sodium alginate, and then beads of this solution were gelled by injecting droplets into a aqueous solution containing calcium chloride. The alginate beads (approximately 3 mm in diameter) were collected, rinsed, and lyophilized. The lyophilized beads were mixed with 85:15 PLGA and NaCl particles and the mixture compression molded and processed with the gas foaming/particulate leaching process as previously described. Following salt leaching and drying, the matrices were placed in serum free tissue culture medium and maintained at 37° C. Medium samples were taken periodically, and analyzed for the content of 125I-VEGF (released from PLGA matrices). The released growth factor was normalized to the total incorporated growth factor.

Results

An initial burst of approximately 20% of the incorporated growth factor was noted in the first day, and a sustained release of growth factor was noted for the remaining 20 days of the experiment (See FIG. 2).

Example 3

Growth Factor Delivery

One factor which may facilitate the development of tissues on the matrices is the delivery of growth factors into the local environment. The incorporation and release of growth factors from these matrices was assessed in vitro using 125I-labeled vascular endothelial growth factor (VEGF). A substantial fraction of the drug was released during the particulate leaching process; however, the remaining drug was released in a sustained manner during the 21 days of the experiment (FIG. 4).

Example 4

Matrix Fabrication

Pellets of poly L-lactic acid [PLLA], a 50:50 copolymer of D,L-lactide and glycolide (50:50 PLGA) with intrinsic viscosity (i.v. of 0.2 dL/g), a 75:25 PLGA copolymer (i.v.= 1.3), and an 85:15 PLGA copolymer (i.v.=1.4) were obtained from Boehringer Ingelheim (Henley, Montvale, N.J., USA). PGA, 50:50 PLGA (i.v.=0.8) and 85:15 PLGA (iv=0.63) were purchased from Medisorb (Cincinnati, Ohio, USA). 85:15 PLGA (i.v.=3.63) was obtained from Purasorb (Lincolnshire, Ill., USA).

The solid polymer (PLLA, PLGA, PGA) was ground (after freezing with liquid nitrogen) using a Scienceware Micro-Mill (Bel-Art Products, Pequannock, N.J., USA) and sieved to a diameter of 106–250 5 m. NaCl, obtained from Fisher Scientific (Pittsburgh, Pa., USA), was sieved to a diameter of 250425 5 m for use in certain experiments. Solid polymer disks were formed by placing 150 mg polymer (PGA, 50:50 PLGA, 75:25 PLGA, 85:15 PLGA, and PLLA) into a round stainless steel KBr die with diameter 1.35 cm (Aldrich Chemical Co., Milwaukee, Wis., USA) and compressing for 60 seconds at 1500 psi in a Carver Laboratory Press (Fred S. Carver, Inc., Menominee Falls, Wis., USA). This method yields solid disks to be foamed. All samples were fabricated in triplicate.

The disks were foamed in a high pressure vessel using $CO_2$, $N_2$, or He at 850 psi. After the disks were equilibrated (1–48 hours) with the gas, the pressure was reduced to ambient. The resulting thermodynamic instability caused nucleation and growth of gas pores within the polymer matrix. 85:15 solid polymer disks (i.v.=1.4) were foamed for 1 hour in $CO_2$ and the pressure was released at different rates (1, 2.5, 5, 10 minutes) to determine if the rate of pressure release affects the final structure of the sponges. All processing steps were performed at ambient temperature.

Polymer/NaCl disks were fabricated in a similar way using 40 mg polymer and 760 mg NaCl, compressed into disks. Following foaming, the disks were placed in distilled water in order to remove the NaCl. This leaching solution was changed several times over the course of about 18 hours. The disks were considered to be completely leeched when the leeching solution did not give a precipitate with AgNO3. If Cl− is present in solution, it precipitates with Ag+ to form a white precipitate. The failure of this precipitate to form indicated that the NaCl is completely removed from the scaffolds. The disks were then air dried overnight, measured and weighed, and stored in a dessicator under vacuum. The polymer disks were measured and weighed immediately following foaming, then stored in a dessicator under vacuum.

Characterization

In order to calculate the porosity of the foamed disks, a boley gauge was used to measure the diameter and thickness of each disk. The disks were weighed on a Mettler balance and the following equation was used: (d=polymer density, g=disk wt, cm3=calculated disk volume).

$$porosity=100[1-(g/cm3)/d]$$

Several of the samples were imaged using a scanning electron microscope (ISI-DS 130, Topcon Technologies, Pleasanton, Calif., USA). The samples were gold coated using a Sputter Coater (Desk II, Denton Vacuum, Cherry Hill, N.J., USA) and the microscope was operated at 10 kV to image the samples. Polaroid 55 film was used for the photomicrographs.

Compression testing was performed on an MTS Bionix 100 (Sintech, Research Triangle Park, N.C., USA). Only polymer/NaCl disks were used in compression tests because the solid polymer disks foamed to irregular shapes. A constant strain rate of 1 mm/min was used, and moduli were determined from the stress-strain curves.

Results

Foaming Solid Polymer Disks

In the first series of experiments, solid polymer disks were foamed to investigate the role of the gas type, pressure release rate, and polymer composition and molecular weight on the porosity of polymer matrices. 85:15 PLGA matrices were foamed for 1 hour with several different gases ($CO_2$, $N_2$, He). Significant porosity resulted from foaming with $CO_2$ as compared to $N_2$ and He. The "prefoam" porosity refers to the calculated porosity following disk preparation, but prior to high pressure equilibration (FIG. 4). Visualization of matrices foamed with $CO_2$ revealed a highly porous matrix consisting largely of closed pores.

In the next study, the rate of release of pressure was varied from 1 to 10 minutes total time. The porosity of the matrices was relatively constant regardless of pressure release rate, except in the case of a very rapid release, when the gas froze within the chamber. This led to a small decrease in the matrix porosity (FIG. 2).

The effect of the polymer composition was investigated by using different copolymer ratios of PLGA (pure PGA, 50:50, 75:25, 85:15 PLGA and pure PLLA). Neither PGA nor PLLA foamed appreciably. The copolymers all foamed to a porosity greater than 90% (FIG. 6). In fact, the 75:25 copolymer foamed so extensively that it did not maintain its integrity in the pressure release/gas expansion phase and literally fell apart. Hence, no porosity value could be calculated for that sample.

In order to study the effect of polymer molecular weight on pore formation, disks of 85:15 PLGA with intrinsic viscosity (i.v.) ranging from 0.63 to 3.59 dL/g were foamed in 850 psi $CO_2$ for 24 hours with a pressure release of 2.5 minutes. The high i.v. PLGA led to matrices with relatively low porosity, whereas the lower i.v. PLGA resulted in much higher porosity (FIG. 7).

Foaming Polymer/NaCl Disks

In the second series of experiments, NaCl was incorporated into the polymer disk for the purpose of creating an open pore structure. Different variables (equilibration time and polymer composition) were studied in order to determine their effects on the structure and stability of the scaffolds. The results of the first series of experiments led us to use $CO_2$ as the foaming gas, and a pressure release time of 2.5 minutes in this series of experiments. Examination of a typical matrix formed by foaming 85:15 PLGA with NaCl in $CO_2$ shows a highly porous structure with largely open, interconnected pores.

In the first study, the equilibration time was varied from 1 to 48 hours. The porosity of the matrices was relatively constant for equilibration times greater than 6 hours, but decreased for equilibration times under 6 hours (FIG. 8a). Matrices fabricated with various equilibration times were subsequently tested to determine if the equilibration time affected their mechanical properties. Even though maximal porosity was achieved with 6 hours of gas equilibration, a stronger scaffold was produced with longer equilibration times (FIG. 8b).

The polymer composition was next varied to determine if results similar to those in the first series of experiments would be obtained. Copolymers of PLG A led to a much greater porosity than did the homopolymers PGA and PLLA (FIG. 9a). Both the PLLA and PGA disks disintegrated in the leaching process, indicating that little, if any, foaming had occurred. Even though all PLGA copolymers led to matrices with similar porosities, the matrices fabricated from PLGA with higher lactic acid content were more rigid (FIG. 9b).

The preceding examples can be repeated with similar success by substituting the generically or specifically described reactants and/or operating conditions of this invention for those used in the preceding examples.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views.

Figure 1:
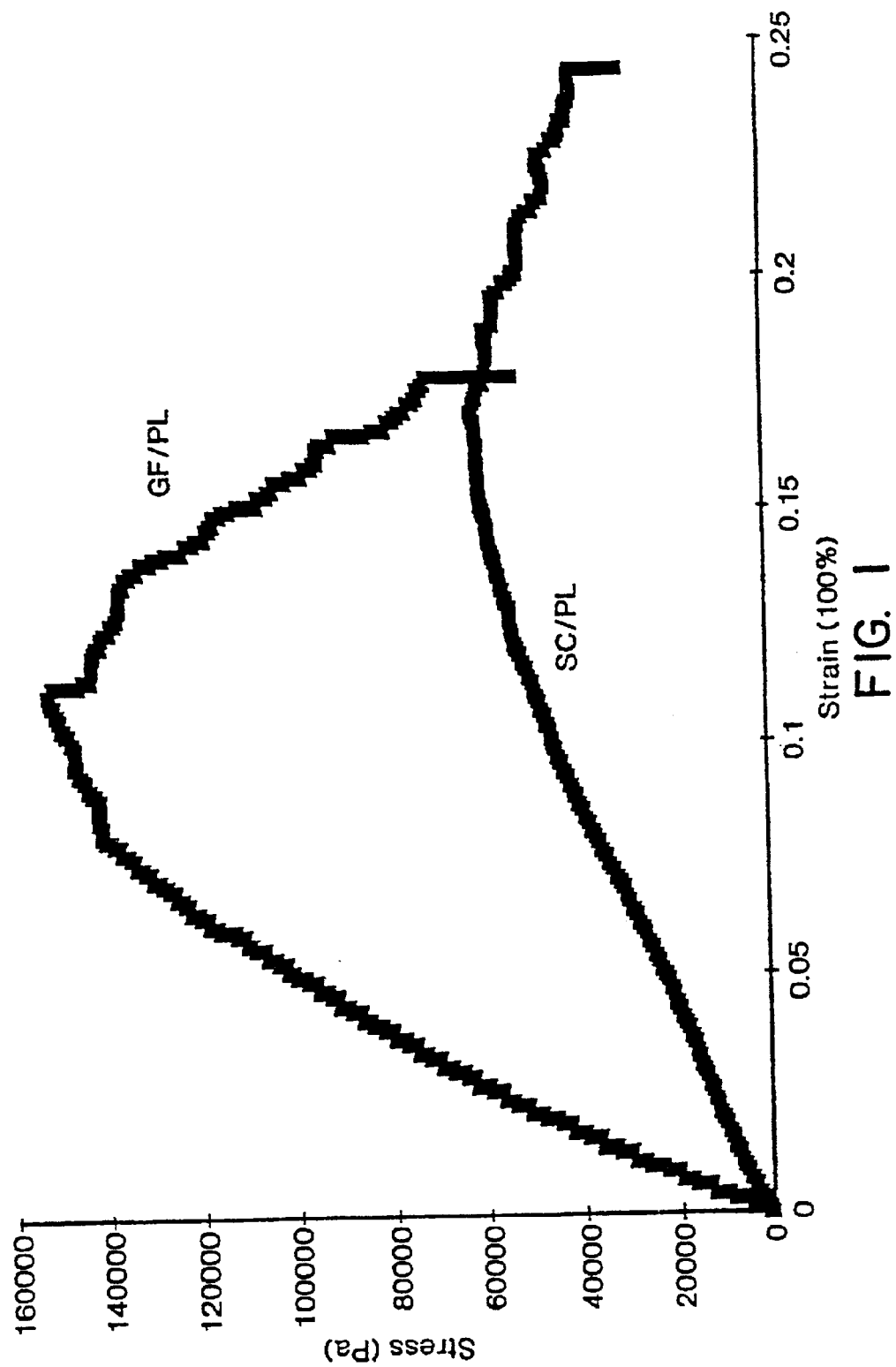
FIG. 1: A graph comparing mechanical properties (tensile strength) of SC/PL and GF/PL matrices.
Figure 2:
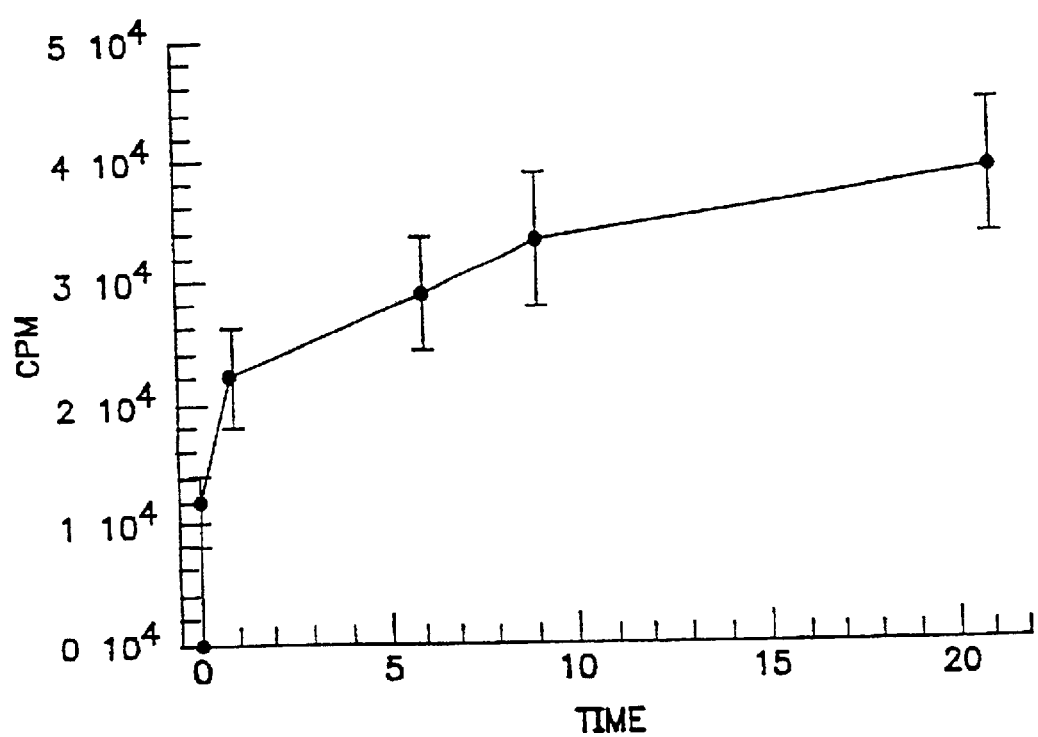
FIG. 2: Shows the release profile of radiolabeled growth factor from the polymer matrix according to Example 2.
Figure 3:
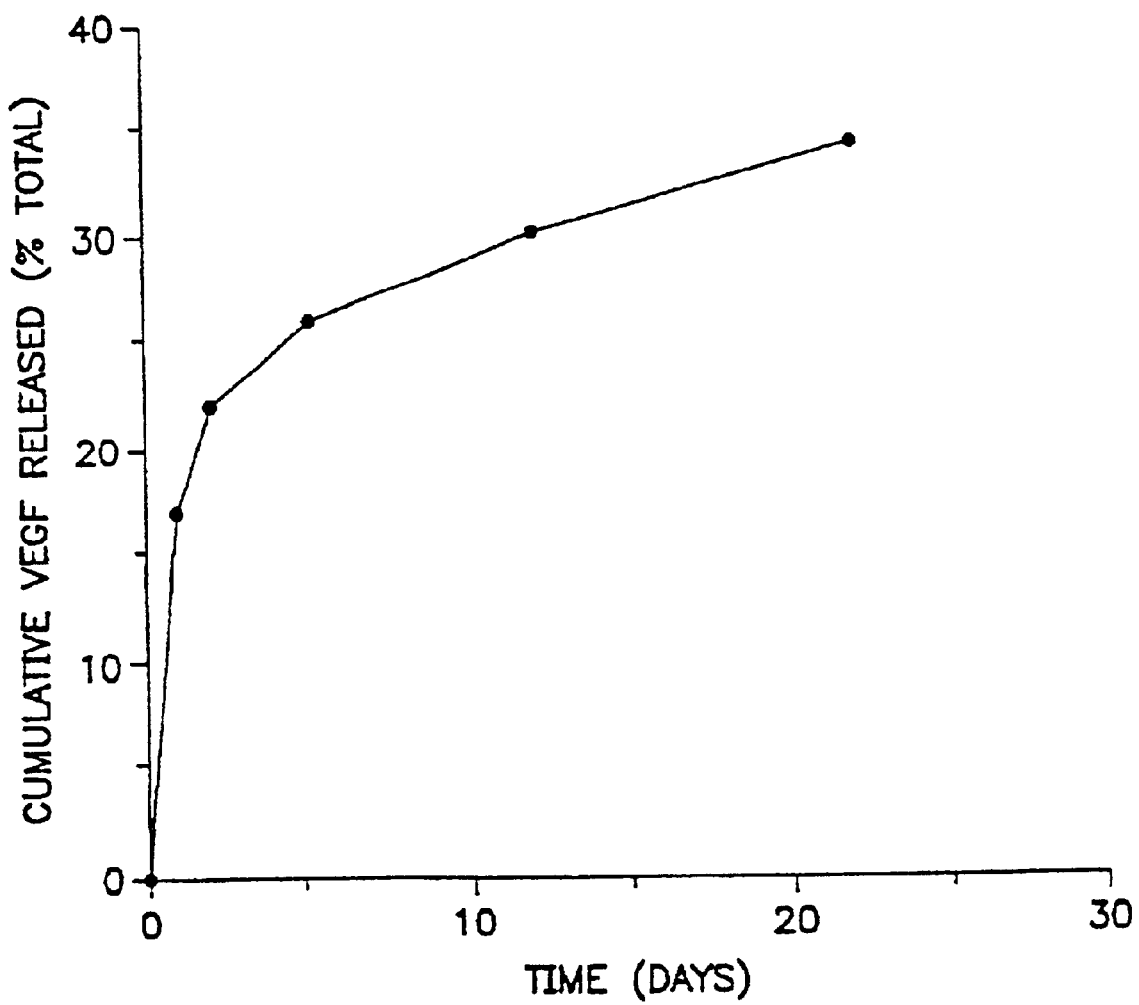
FIG. 3: Shows the cumulative VEGF release over time for the matrix according to Example 3.
Figure 4:
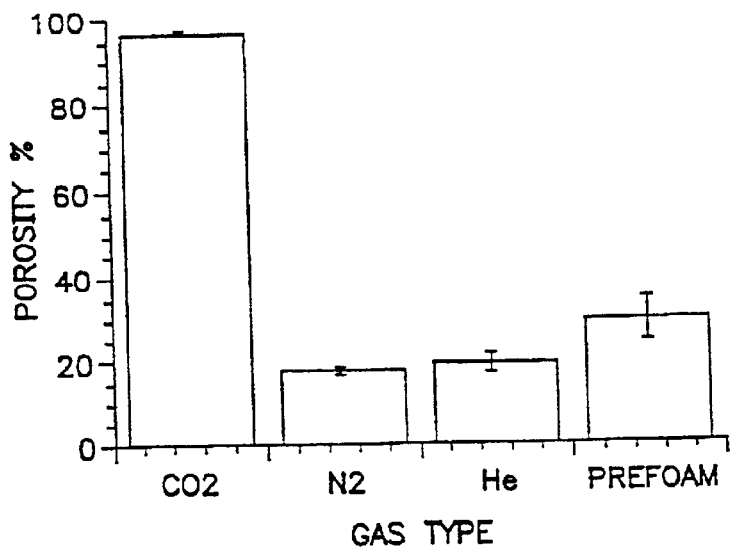
FIG. 4: The effect of gas type on porosity of matrices. 85:15 PLGA (i.v.=1.4 dL/g) disks were equilibrated for 1 hour in 850 psi gas prior to pressure The time for pressure release was 2.5 minutes.
Figure 5:
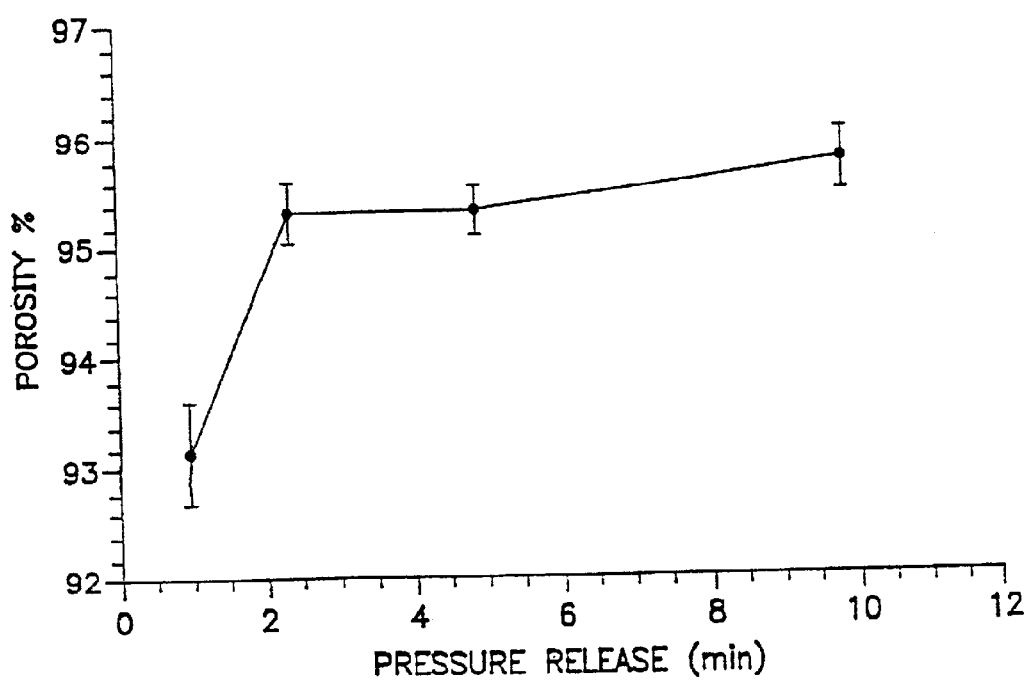
FIG. 5: The effect of pressure release rate on porosity of PLGA matrices. 85:15 PLGA (i.v.=1.4) disks were foamed for 1 hour in $CO_2$, with a pressure release time of 1 to 10 minutes.
Figure 6:
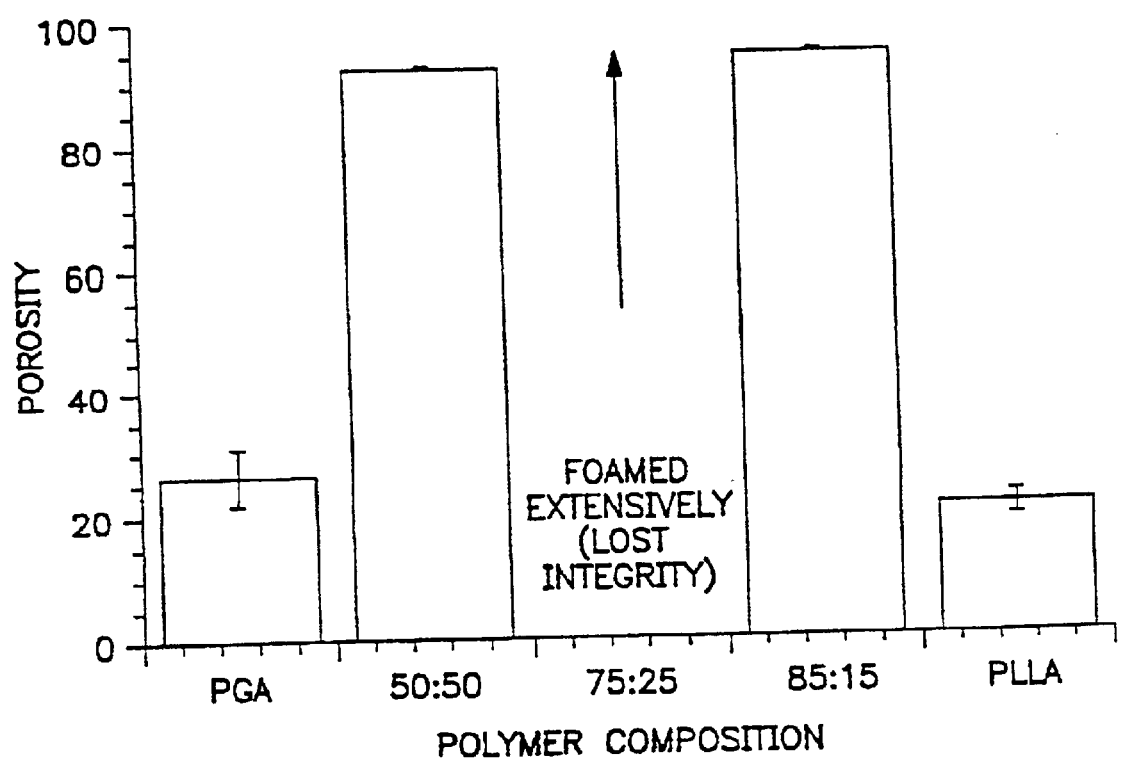
FIG. 6: Porosity of matrices fabricated from different polymers. Polymers were exposed to 850 psi $CO_2$ for 24 hours with pressure release of 2.5 minutes.
Figure 7:
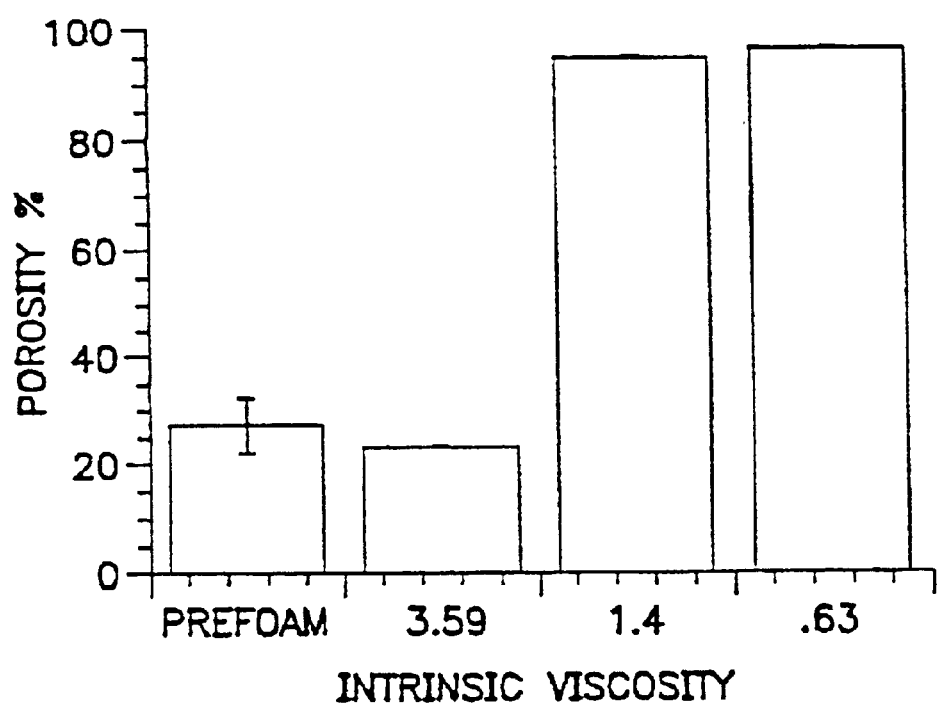
FIG. 7: The effect of molecular weight on porosity of PLGA matrices. Matrices of 85:15 PLGA with varied intrinsic viscosity were foamed for 24 hours in 850 psi $CO_2$ with a pressure release time of 2.5 minutes.
Figure 8A:
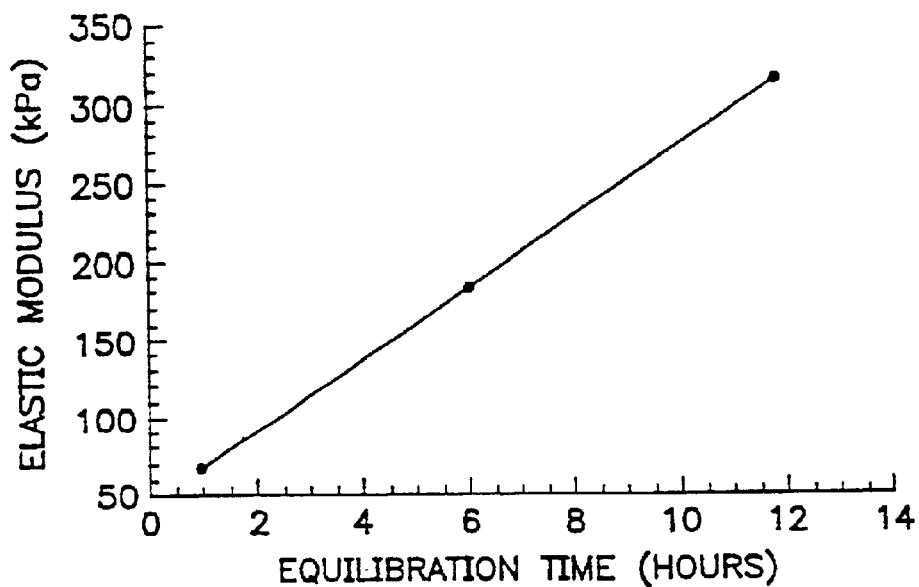
FIG. 8a: Porosity of matrices with varied equilibration times. 85:15 PLGA (i.v.=1.4) and NaCl disks were foamed in 850 psi $CO_2$ for time ranging from 1–48 hours. The pressure release time was 2.5 minutes.
Figure 8B:
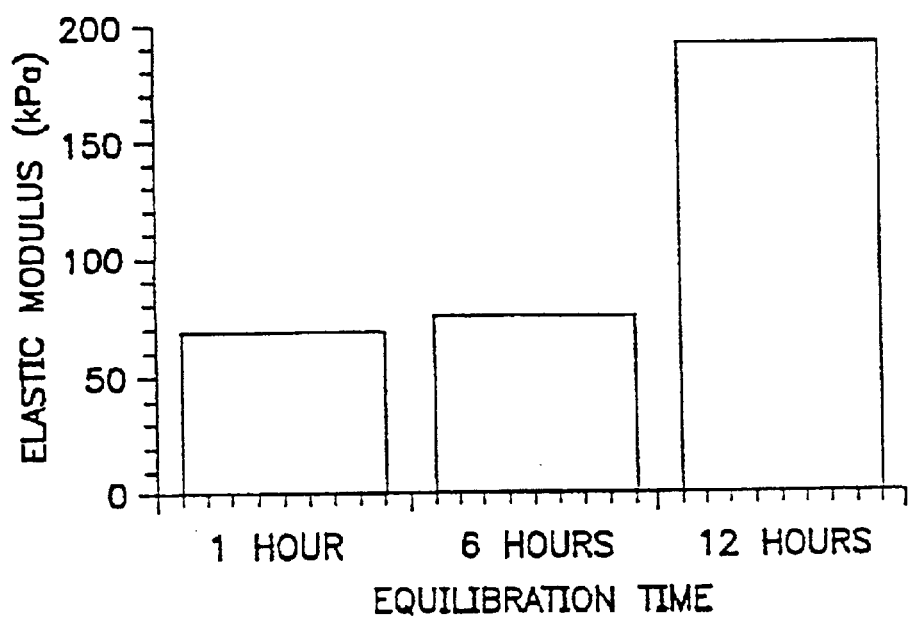
FIG. 8b: The elastic modulus of polymer/NaCl scaffolds fabricated with different equilibration times. 85:15 PLGA (i.v.=1.4)/NaCl disks were foamed in 850 psi $CO_2$ for 1–12 hours with 2.5 minute pressure release.
Figure 9A:
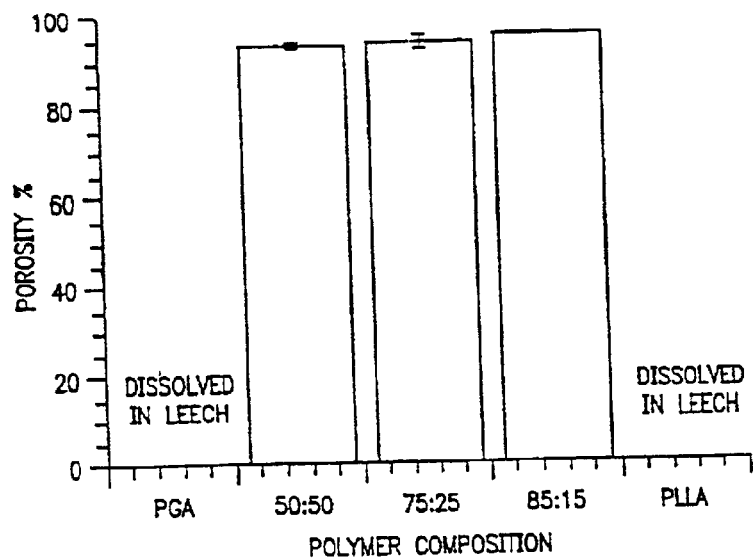
FIG. 9a: The effect of polymer composition on porosity of polymer/NaCl scaffolds. Different copolymers of PLGA, PGA, and PLLA with NaCl were foamed for 24 hours in 850 psi $CO_2$ with a pressure release time of 2.5 minutes.
Figure 9B:
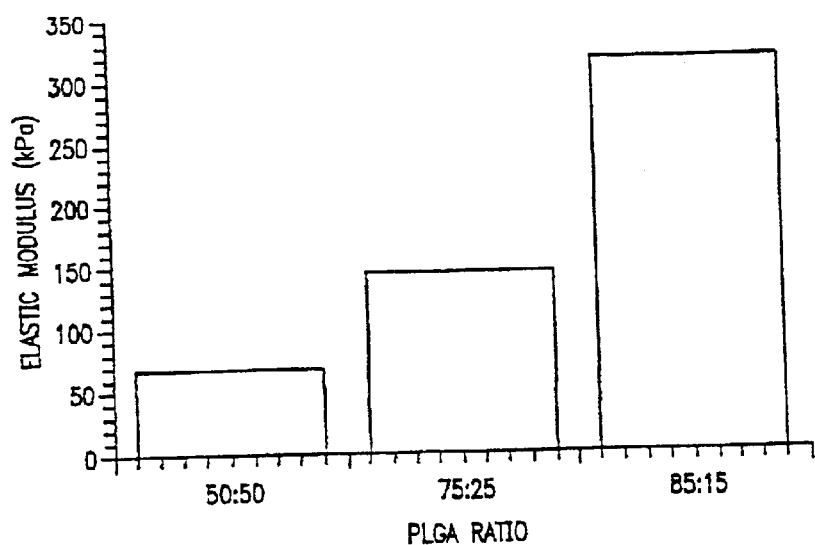
FIG. 9b: The elastic modulus of matrices formed with different polymer compositions. Different copolymer ratios of PLGA with NaCl were foamed for 24 hours in 850 psi $CO_2$ with 2.5 minute pressure release.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a porous biocompatible polymer material which comprises forming pores in a biocompatible polymer material which contains a leachable particulate by gas foaming and subsequently leaching out the particulate material to form additional porosity.

2. The process of claim 1, wherein formation of the pores by gas foaming is conducted by subjecting a mixture of particles of the polymer and particles of the particulate to an elevated pressure atmosphere of an inert gas such that the gas dissolves into the polymer and then creating a thermodynamic instability such that nucleation and growth of gas pores occurs and the polymer containing the particulate forms a continuous matrix.

3. The process of claim 2, wherein the mixture of particles of the polymer and particles of the particulate is compression molded into a selected size and shape before formation of the gas pores.

4. The process of claim 2, wherein the thermodynamic instability is created by reduction of the pressure atmosphere.

5. The process of claim 2, wherein the gas is $CO_2$.

6. The process of claim 1, wherein the polymer is a biocompatible and biodegradable polymer.

7. The process of claim 1, wherein the polymer is a homopolymer or copolymer of lactic acid and/or glycolic acid.

8. The process of claim 1, wherein the polymer is PLGA.

9. The process of claim 1, wherein the polymer is a blend of a homopolymer or copolymer of lactic acid and/or glycolic acid with another polymer.

10. The process of claim 9, wherein the polymer is a blend of a homopolymer or copolymer of lactic acid and/or glycolic acid with an alginate polymer.

11. The process of claim 1, wherein the particulate is a water-soluble particulate.

12. The process of claim 1, wherein the particulate is a salt.

13. The process of claim 1, wherein the particulate is NaCl.

14. The process of claim 1, wherein the size and amount of the particulate is selected such that an interconnected pore structure in the porous polymer material is formed.

15. The process of claim 12, wherein the amount of particulate is at least 50% by volume of the mixture of particles of the polymer and particles of the particulate.

16. The process of claim 12, wherein the average particle size of the particulate is from 10 to 500 microns.

17. A porous biocompatible polymer comprising a biocompatible polymer matrix containing pores formed by gas foaming and pores formed by leaching out of a particulate from the polymer.

18. The polymer of claim 17, wherein the polymer matrix is a biocompatible and biodegradable polymer.

19. The polymer of claim 17, wherein the polymer matrix is a homopolymer or copolymer of lactic acid and/or glycolic acid.

20. The polymer of claim 17, wherein the polymer matrix is PLGA.

21. The polymer of claim 17, wherein the polymer has an interconnected pore structure.

22. The polymer of claim 17, wherein the combination of pores provides a uniform open pore structure.

23. The polymer of claim 17, wherein the polymer exhibits a tensile modulus of 850 kPa or higher.

24. A method for drug delivery which comprises introducing a drug contained within a porous biocompatible polymer of claim 17.

25. A method for drug delivery according to claim 24, wherein the drug is a growth factor contained within the polymeric structure of a polymer bead which is contained within the porous biocompatible polymer.

26. A method for tissue engineering which comprises introducing as a matrix for the tissue a porous biocompatible polymer of claim 17.

27. A method for cell transplantation comprising administering a combination of a porous biocompatible polymer of claim 17 and cells for transplantation.

28. A method for cell culturing which comprises culturing cells in the pores of a porous biocompatible polymer of claim 17.

29. A polymer material which comprises a section of porous biocompatible polymer comprising a polymer matrix containing pores formed by gas foaming and pores formed by leaching out of a particulate from the polymer and a section of impermeable polymer integrally connected.

30. The polymer material of claim 29, wherein the porous biocompatible polymer has a uniform open pore structure and the impermeable polymer is of the same polymer material but without an open pore structure.

31. A method for guided tissue regeneration which comprises introducing to the location requiring tissue regeneration a polymer material according to claim 29.

32. The polymer material of claim 29, wherein the porous biocompatible polymer and the impermeable polymer are of different polymer material.

33. The polymer of claim 17, which further comprises a drug contained within the pores of the porous biocompatible polymer.

34. The polymer of claim 17, which further comprises viable cells within the pores of the porous biocompatible polymer.

35. The polymer material of claim 27, which further comprises, within the pores of the section of porous biocompatible polymer, viable cells for tissue regeneration.

* * * * *